(12) United States Patent
von Falkenhausen

(10) Patent No.: US 6,586,040 B1
(45) Date of Patent: Jul. 1, 2003

(54) METHOD FOR MANUFACTURING A LAMINATE CONSISTING OF INDIVIDUAL LAYERS

(75) Inventor: Christian von Falkenhausen, Bonn (DE)

(73) Assignee: LTS Lohmann Therapie-Systeme AG (DE)

( * ) Notice: Subject to any disclaimer, the term of this patent is extended or adjusted under 35 U.S.C. 154(b) by 0 days.

(21) Appl. No.: 09/719,488

(22) PCT Filed: Jun. 7, 1999

(86) PCT No.: PCT/EP99/03905

§ 371 (c)(1),
(2), (4) Date: Feb. 12, 2001

(87) PCT Pub. No.: WO99/65472

PCT Pub. Date: Dec. 23, 1999

(30) Foreign Application Priority Data

Jun. 15, 1998 (DE) .......................................... 198 26 592

(51) Int. Cl.$^7$ .............................. B05D 3/00; B05D 7/04; B05D 5/10; B05D 1/36; B05D 1/38
(52) U.S. Cl. ..................... 427/2.31; 427/2.1; 427/413; 427/417; 427/411; 427/412.1; 427/407.1; 427/258; 427/261
(58) Field of Search .............................. 427/2.31, 417, 427/413, 407.1, 411, 412.1, 2.1, 258, 261

(56) References Cited

U.S. PATENT DOCUMENTS

| | | | | |
|---|---|---|---|---|
| 4,485,087 A | * | 11/1984 | Otsuka et al. ................. 424/28 |
| 4,564,010 A | * | 1/1986 | Coughlan et al. ........... 128/156 |
| 4,769,028 A | * | 9/1988 | Hoffmann et al. .......... 424/443 |
| 4,900,552 A | | 2/1990 | Sanvordeker et al. | |
| 5,089,205 A | * | 2/1992 | Huang et al. ................ 264/255 |
| 5,567,489 A | * | 10/1996 | Allen et al. ................. 428/34.1 |
| 5,569,484 A | | 10/1996 | Muller et al. | |
| 5,730,919 A | * | 3/1998 | Wilfong et al. ........ 264/173.11 |
| 5,902,601 A | | 5/1999 | Horstmann | |
| 6,010,715 A | * | 4/2000 | Wick et al. .................. 424/448 |
| 6,096,378 A | * | 8/2000 | Komatsu et al. ......... 427/407.1 |
| 6,106,902 A | * | 8/2000 | Koskinen et al. ............ 427/424 |
| 6,287,634 B1 | * | 9/2001 | Beall et al. .................. 427/220 |

FOREIGN PATENT DOCUMENTS

| | | | |
|---|---|---|---|
| DE | 3315272 | 9/1988 | |
| DE | 42 30 589 | 10/1996 | |
| DE | 4332094 | 5/1999 | |
| DE | 197 15 794 | 10/2001 | |
| EP | 0050480 | 4/1982 | |
| EP | 0-262753 A1 | * 4/1988 | .......... A61M/37/00 |
| EP | 0262753 | 4/1988 | |
| EP | 0593807 | 4/1994 | |
| EP | 0593807 | 7/1994 | |
| WO | WO 89/07429 | 8/1989 | |
| WO | WO 95/24172 | 9/1995 | |
| WO | WO 97/35564 | 10/1997 | |

OTHER PUBLICATIONS

Heilman, K., *Therapeutische Systeme—Konzept und Realisation programmeierte Arzneiverabreichung*, "Therapeutische Systeme für systemische Anwendung", pp. 48–53, 4$^{th}$ Edition, 1984.

"Transdermal Controlled System Medications;" Chien, Yie W.; Controlled Drug–Delivery Research Center Rutgers –The State University of New Jersey; Marcel Dekker, Inc.; 1987; Chapter 14, pp. 365–378.

* cited by examiner

*Primary Examiner*—Bret Chen
*Assistant Examiner*—Jennifer Kolb Michener
(74) *Attorney, Agent, or Firm*—D. Peter Hochberg; Katherine R. Vieyra; Sean Mellino

(57) ABSTRACT

A process for producing a laminate comprising individual layers, such process including a sequence of operations in which initially a support substrate is provided, to which at least two compositions, each of which is liquid under the processing conditions, are applied as individual layers, one on top of the other. Each composition comprises either one active pharmaceutical or cosmetic substance or one pharmaceutical or cosmetic auxiliary.

20 Claims, No Drawings

METHOD FOR MANUFACTURING A LAMINATE CONSISTING OF INDIVIDUAL LAYERS

BACKGROUND OF THE INVENTION

The invention relates to a process for producing a laminate comprising individual layers, comprising a sequence of operations in which first a support substrate is provided, to which a composition which is flowable under processing conditions is applied as a layer, to which layer subsequently at least one further composition which is flowable under processing conditions is applied as a layer.

BACKGROUND OF THE INVENTION

Laminates are multilayer sheetlike materials. Laminates in the form of plasters for application to the skin generally comprise at least one film and at least one pressure sensitively adhering layer. In the context of the invention, the term "laminate" denotes a structure comprising individual layers, in some cases none of these layers comprising a film. In accordance with the prior art, multilayer laminates are normally produced by joining individual single-ply layers. A layer of this kind is produced by first providing a support substrate, generally in the form of a dehesively treated film, which is then coated with a "liquid", i.e., solvent-containing, polymer composition. Subsequent drying of the coated substrate brings about evaporation of the solvent and, with it, crosslinking of the polymer chains in the applied layer. The dried polymer layer can then be lined with a removable film.

Following the abovementioned operations, a multilayer laminate is produced by joining two or more single-ply layers, the cover film of each individual layer being discarded.

The known production process is disadvantageous in a number of respects. First of all, it is necessary to produce individual layers in a sequence of operations and then to join these layers. Since, moreover, the cover films of each layer are discarded, the process is profligate in its use of materials.

Furthermore, the incorporation of volatile active substances and/or auxiliaries into solvent-containing compositions leads, during the drying of each layer and/or of the laminate, to the evaporation of a—in certain instances considerable—fraction of the substances incorporated. Overall, the customary coating process associated with the production of a multilayer laminate is uneconomic and costly, and in some cases even unsuitable, for the majority of the active substances and auxiliaries of this class of substance.

SUMMARY OF THE INVENTION

The invention is based on the object of specifying a process for producing a laminate comprising individual layers, which process avoids the abovementioned disadvantages and difficulties, is suitable for an economically advantageous production of laminates comprising pharmaceutical and/or cosmetic ingredients, and minimizes evaporative losses on drying and the consumption of cover film material.

A more particular object of the invention is to provide a process for producing a laminate comprising individual layers, such process including a sequence of operations in which initially a support substrate is provided, to which at least on e composition which is liquid under the processing conditions is applied as a layer.

DESCRIPTION OF THE PREFERRED EMBODIMENTS

To this end, a first composition, which is in a flowable state, is applied in the form of a first layer to the solid substrate acting as support, and at least one further composition, which is likewise in a flowable state, is applied in the form of a further layer to this first composition, which is in the form of a layer and is in a flowable state.

The multilayer laminate thus produced may subsequently be freed from solvent residues by means of extremely careful drying. In this way, the individual compositions which are in the form of layers and are in a flowable state undergo transition to a nonflowable state, e.g., a solid state. Moreover, this may take place not only by drying but also by chemical crosslinking of individual components of the compositions in layer form or by solidification as a result of cooling of an essentially solvent-free flowable composition. A flowable state, which in the context of the invention is to be equated with the term "liquid", means the state in which the composition possesses a consistency in which it is capable of a change in shape. In this sense, therefore, melts, solutions, dispersions, suspensions, conglomerates, etc., of substances, e.g., macromolecular substances, in particular, may also be present in a flowable state. This state, which describes the flowability of a system, is characterized by the skilled worker by indicating, inter alia, the viscosity. The individual compositions used in the production process described possess a dynamic viscosity,[mpa s] in the range from 1 to 500,000, preferably between 50 and 10,000, for solvent-containing substances or between 500 and 250,000 for melts (hotmelts), and with particular preference between 500 and 5,000 for solvent-containing substances, or between 800 and 15,000 for melts (hotmelts). After the conclusion of the process of the invention, the compositions of the individual layers are in a nonflowable state, e.g., in the solid state. This means that the compositions, although they may still possess a certain elasticity, are no longer capable of a permanent change in their layer shape.

The process according to the invention makes it possible to produce multilayer laminates with one operation per layer, without a backing film and/or cover film, thereby significantly reducing machine running times and material costs.

The omission of an intermediate drying stage makes for an at least considerable reduction in the costly use of solvents and drying energy, and minimizes the amount of time taken up by production. Through appropriate formulations of the individual coating compositions, it is also possible to produce laminates having specific properties while reducing the manufacturing steps required when applying each layer. For example, the first layer may comprise a volatile active substance and/or auxiliary, whereas the formulation of the following layer remains free of active substance. During the drying operation, this latter layer acts as a barrier layer for the active substance present in the first layer. Accordingly, it is easier to produce laminates comprising volatile active substances and auxiliaries. For this purpose it is possible with advantage to adopt the measure of applying layers on top of one another without drying beforehand, "liquid on liquid". Further embodiments of the process are envisaged in accordance with the features of the subclaims. One embodiment envisages using a solvent-containing composition to apply a layer. For the application of a layer it is also possible, however, to use a composition comprising at least one crosslinkable constituent.

Furthermore, one embodiment of the, process envisages drying the laminate after applying a final layer. Compositions comprising the same kind of constituents may be used for individual layers to be applied to the substrate. Alternatively, compositions comprising constituents of the same kind except for one constituent may be used for applying layers intended for application to the substrate. The invention is also not intended to rule out the coating of a layer with a solvent content of at least 10% with a further layer. For this purpose, it is possible to use compositions which differ with regard to their density and/or viscosity and/or crosslinkability and/or solids content and/or solvent content and/or pH. It is also possible to apply layers differing in thickness, or to choose the same or different coating widths of individual layers. The invention also embraces the possibility of using a single-layer or multilayer substrate as the laminate's support. Additionally, multiple coating of the substrate may be carried out by means of different application and metering techniques, e.g., by means of blade metering, roller matering, flow or curtain metering, hot-melt coating techniques, or a combination of these techniques. Finally, the production of layers by printing techniques, including pad printing or screen printing techniques, may also be envisaged in accordance with the process of the invention. In principle there is no restriction on the thickness of the layers which may be produced from the compositions which are present in the flowable state. In connection with the process of the invention, this thickness is essentially between 1 and 500 µm, preferably between 10 and 200 µm. An upper limit on the thickness of the layer, however, may depend under certain circumstances on the degree of flowability of the compositions which are present in the flowable state. In the case of compositions having good flowability (low viscosity, i.e. relatively mobile, for example; capable of a change in shape without application of great external force), there may occasionally exist such an upper limit on the thickness of the layer. The skilled worker, however, knows what measures to take to influence the flowability of the composition. For example, a reduction in the melting temperature and/or a reduction in the solvent content of the solution (or suspension or dispersion) and/or the greater crosslinking of a polymer material generally lead to a reduction in flowability. Such measures may have to be carried out in order to vary the flowability of the compositions in such a way that they can be used to produce layers of desired thickness. If, however, a composition possesses very poor flowability (high viscosity, i.e., relatively viscous, for example), then the flowability of the composition should be improved by increasing the melting temperature and/or increasing the solvent content of the solution and/or by reduced crosslinking of a polymer material and/or by application of relatively high external force (e.g., by means of pressure) during lamination.

The process of the invention is especially suitable for producing active substance laminates for topical application in the form of plasters most especially in the field of transdermal medication. Furthermore, the process also makes it possible to produce active substance laminates which are not intended for topical application, such as administration forms in the form of films or foils, for example.

Coating compositions of individual layers may comprise rubber, rubberlike homopolymers, copolymers or block copolymers, silicones, polyacrylates and copolymers thereof, polyurethane, copolymers of ethylene, polysiloxanes, etc. as their polymer material. Auxiliaries may also be included, which customarily take on functions as plasticizers, tackifiers, absorption promoters, stabilizers, or fillers. The chemical crosslinking of a macromolecular substance, i.e., of a polymer, takes place with the aid of what are known as crosslinkers, which are known to the skilled worker. These substances generally possess at least two functional groups and cause chainlike polymer molecules to acquire a three-dimensional structure in the course of chemical crosslinking. The specific substances suitable for this purpose are dependent on the nature of the polymer.

Laminates used in accordance with the invention, for application to the skin, for example, are single-layer or multilayer laminates whose materials are of a kind such that they are suitable for prolonged wearing on the skin. They include known tapes such as Hansaplast®, Leukosilk®, Leukoplast®, and active substance plaster materials such as transdermal therapeutic systems (TTS), which are described, for example, in K. Heilmann "Therapeutische Systeme—Konzept und Realisation programmierter Arzneiverabreichung" [Therapeutic Systems—Design and Realization of Programmed Drug Administration] (4th Edition, 1984). They generally comprise a backing layer, a single-layer or multilayer matrix, and a removable protective layer. The backing layer may comprise flexible or inflexible material. Substances which are used to produce them are polymeric substances, such as polyethylene, polypropylene, polyethylene terephthalate, polyurethane or polyamide, for instance. Further suitable materials include polyvinyl alcohol, styrene-diene block copolymers, polyvinyl chloride, and polymethacrylates, to name but a few examples. Combinations of the materials mentioned may also be used. Examples of further materials which can be used are films vapor coated with aluminum, on their own or coated with a polymeric substrate.

For removable protective films, it is possible in principle to use the same materials, with the proviso that they must additionally have been treated to render them adhesive. This can be achieved, for example, by siliconization. The reservoir and/or the matrix, which may be single-layer or multilayer in design, generally comprise auxiliaries as additives, in addition to one or more active substances. Suitable substances include polymers such as polyisobutylene, esters of polyvinyl alcohol, polyacrylates and polymethacrylates, natural rubber, styrene, isoprene, and styrene-butadiene polymers, silicone polymers, resin constituents such as saturated or unsaturated hydrocarbon resins, derivatives of abietyl alcohol and of β-pinene, plasticizers such as phthalates, triglycerides, and fatty acids. The polymer material of the matrix may also have been synthesized from polymers such as rubber, rubberlike synthetic homopolymers, copolymers or block polymers, polyurethanes, copolymers of ethylene, or polysiloxanes.

The additives mentioned—also called auxiliaries—are classified according to their function as plasticizers, tackifiers, absorption promoters, stabilizers, or fillers. Such substances, which must be physiologically unobjectionable, are known to the skilled worker. For the laminates used in the process of the invention, especially for those from which TTS are produced, it is possible with preference to use active pharmaceutical substances able to pass through the skin. Such substances are present, for example, in the active substance groups of the parasympatholytics, e.g., scopolamine, atropine, benactyzine, the cholinergics, e.g., physostigmine, nicotine, the neuroleptics, e.g., chlorpromazine, haloperidol, the monoamine oxidase inhibitors, e.g., tranylcypromine, selegiline, the sympathomimetics, e.g., ephedrine, D-norpseudoephedrine, salbutamol, fenfluramin, the sympatholytics and antisympathotonics, e.g., propranolol, timolol, bupranolol, clonidine, dihydroergotamine, naphazoline, the anxiolytics, e.g., diazepam, triazolam, the local anesthetics, e.g., lidocaine, the central analgesics, e.g., fentanyl, sufentanil, the antirheumatics, e.g., indomethacin, piroxicam, lornoxicam, the coronary therapeutics, e.g., glycerol trinitrate, isosorbide dinitrate, the oestrogens, gestagens and androgens, the antihistamines, e.g., diphenhydramine, clemastine, terfenadine, the prostaglandin derivatives, the vitamins, e.g., vitamin E, cholecalciferol, and the cytostatics.

With the process of the invention, especially the process of the "liquid on liquid" coating of compositions comprising ingredients comprising active substances and/or auxiliaries, it is possible to prepare multilayer laminates in a closed sequence of extremely economic production processes. With great advantage it is possible in particular to produce laminates which comprise volatile active substances and/or auxiliaries. Accordingly, the invention provides an optimum solution to The invention has been described with particular emphasis on the preferred embodiments, but variations and modifications within the spirit and scope of the invention may occur to those skilled in the art to which the invention pertains.

What is claimed is:

1. A process for producing a multilayer laminate suitable for use as a pharmaceutical administration form, said laminate comprising individual layers, said process comprising the following sequence of operations:

providing a support substrate, applying at least one flowable coating composition to said substrate as a first layer, and subsequently, while said first layer is in a flowable state, applying to said first layer at least one further flowable coating composition as a further layer or layers, and finally subjecting said layers to a process selected from the group consisting of drying and chemical crosslinking, to solidify the layers;

wherein at least one of said first layer and said further layer(s) comprises at least one substance selected from the group consisting of active pharmaceutical substances, active cosmetic substances, pharmaceutical auxiliaries and cosmetic auxiliaries, and wherein at least one layer of said multilayer laminate comprises an active substance, and at least one further layer is applied onto said layer.

2. The process as claimed in claim 1, wherein at least one layer of said multilayer laminate comprises an active substance, and at least one further layer lacking an active substance is applied onto said layer.

3. The process as claimed in claim 1, wherein the step of applying one layer comprises applying a flowable composition comprising at least one solvent to at least one of said substrate, said first layer, and one of said further layers.

4. The process as claimed in claim 1, further comprising a step of forming an emulsion of two mutually immiscible solvents, said emulsion being used as said coating composition.

5. The process as claimed in claim 1, wherein one of said layers is a pressure sensitive adhesive.

6. The process as claimed in claim 1, wherein the step of applying one layer comprises applying a flowable coating composition comprising at least one crosslinkable constituent.

7. The process as claimed in claim 1, further comprising the step of drying the lamination following the application of a final layer of the process set forth in claim 1.

8. The process as claimed in claim 1, wherein at least two of the operations of applying coating compositions comprise applying identical constituents as the layers.

9. The process as claimed in claim 1, wherein the operation of applying coating compositions comprises applying coating compositions which are identical, with the exception of said active substance.

10. The process as claimed in claim 1, wherein one layer of said multilayer laminate has a solvent content of at least 10% and is coated with a second layer.

11. The process as claimed in claim 1, wherein the coating compositions differ with respect to at least one of their density, viscosity, crosslinkability, solids content, solvent content, and pH.

12. The process as claimed in claim 1, wherein layers differing in thickness are applied.

13. The process as claimed in claim 1, wherein individual layers are selected with the same or different coating widths.

14. The process as claimed in claim 1, wherein a single-layer or multilayer substrate is used.

15. The process as claimed in claim 1, wherein multiple coating of the substrate is carried out by means of different application and metering techniques.

16. The process as claimed in claim 1, wherein layers are produced by a technique selected from the group consisting of a printing technique and a hot-melt application technique.

17. The process as claimed in claim 2, wherein the layer without active substance is a barrier layer.

18. The process as claimed in claim 1, wherein said one further layer is applied to said one layer while both of said layers are liquid.

19. The process as claimed in claim 16, wherein the process is selected from the group consisting of pad printing and screen printing.

20. The process as claimed in claim 1, wherein a further layer is applied to one of said layers without drying said one layer beforehand.

* * * * *